United States Patent [19]

Hui et al.

[11] Patent Number: 5,082,656
[45] Date of Patent: Jan. 21, 1992

[54] TOPICAL ANTIBACTERIAL COMPOSITIONS CONTAINING PENETRATION ENCHANCERS

[75] Inventors: Ho-Wah Hui, Vernon Hills; Chung-Chiang Hsu, Libertyville; Madhu K. Vadnere, Grayslake, all of Ill.

[73] Assignee: Abbott Laboratories, Abbott Park, Ill.

[21] Appl. No.: 444,491

[22] Filed: Dec. 1, 1989

Related U.S. Application Data

[63] Continuation of Ser. No. 108,175, Oct. 13, 1987, abandoned, which is a continuation-in-part of Ser. No. 44,521, Apr. 30, 1987, abandoned.

[51] Int. Cl.⁵ ............... A61K 31/79; A61K 31/74
[52] U.S. Cl. ............... 514/24; 514/29; 514/152; 514/620; 514/772.5; 514/772.6
[58] Field of Search ............... 424/78, 80

[56] References Cited

U.S. PATENT DOCUMENTS

| | | | |
|---|---|---|---|
| 2,970,081 | 1/1961 | McCall et al. | 167/30 |
| 3,791,983 | 2/1974 | Maierson | 424/78 |
| 3,862,309 | 1/1975 | Krockrok | 424/78 |
| 4,492,685 | 1/1985 | Keith et al. | 424/28 |
| 4,692,328 | 9/1987 | Kitchell et al. | 424/78 |
| 4,695,453 | 9/1987 | Tuominen et al. | 424/82 |
| 4,769,013 | 9/1988 | Lorenz et al. | 604/265 |
| 4,810,489 | 3/1989 | Murray et al. | 424/59 |
| 4,917,883 | 4/1990 | Strobridge | 424/59 |

FOREIGN PATENT DOCUMENTS

| | | |
|---|---|---|
| EP85334 | 8/1983 | European Pat. Off. . |
| 2047874 | 9/1971 | France . |
| WO8605391 | 9/1986 | World Int. Prop. O. . |

OTHER PUBLICATIONS

Chem. Abstr. 100:215535x (JP5929615).
R. Oteri et al., Cosmetics and Toiletries, 102, 107 (1987).

*Primary Examiner*—Thurman K. Page
*Assistant Examiner*—Peter F. Kulkosky
*Attorney, Agent, or Firm*—Steven R. Crowley

[57] ABSTRACT

An antibacterial composition for topical administration, comprising from about 0.5 to about 10 percent of an antibacterial compound; from about one to about 30 percent of a non water soluble polymeric composition; from about 0.5 to about 40 percent of a plasticizer which plasticizes and polymeric composition; and from about 50 to about 95 percent of a solvent in which said polymeric composition and plasticizer are dissolved; whereby upon topical application of said antibacterial composition, said solvent will evaporate or penetrate the skin and leave a thin protective film of polymeric composition which retains said antibacterial compound against the skin.

11 Claims, No Drawings

TOPICAL ANTIBACTERIAL COMPOSITIONS CONTAINING PENETRATION ENCHANCERS

BACKGROUND OF THE INVENTION

This is a continuation of application Ser. No. 108,175, filed Oct. 13, 1987, now abandonded, which is a continuation-in-part of U.S. Ser. No. 044,521 filed Apr. 30, 1987, now abandoned.

This invention relates to topical antibacterial compositions.

There are many topical indications for antibacterial compounds. One important indication is acne. Many compositions including antibacterial compounds have been formulated for topical administration, but they have certain deficiencies. Some are water soluble so they are diluted by perspiration, or can be completely washed or worn off with water when the user swims or showers, for example. Thus, the water soluble compositions must be frequently applied. Other compositions do not penetrate very well into the skin, which is a requisite for some antibacterial compounds to be effective.

SUMMARY OF THE INVENTION

The topical antibacterial composition of this invention effectively penetrates the skin. At the same time, the composition resists washing and wear.

The antibacterial composition includes from about one to about 30 percent of a non-water soluble polymeric composition; from about 0.5 to about ten percent of an antibacterial compound; from about 0.5 to about forty percent of a plasticizer; and from about fifty to about ninety-five percent of a solvent in which said polymeric composition can be dissolved or dispersed. The polymeric composition retains the antibacterial compound on the skin, and forms a water and wear resistant film when the antibacterial composition is applied to the skin. The plasticizer prevents the film from cracking on the skin. Finally, the solvent allows the antibacterial composition to be easily applied, yet it evaporates and/or is absorbed into the skin, to leave a wear and water resistant film on the skin.

TECHNICAL DISCLOSURE

The antibacterial composition of the present invention is for topical application. It includes from about one to about 30 percent of a non water soluble polymeric composition, and from about 0.5 to about ten percent of an antibacterial compound. From about 0.5 to about forty percent of a plasticizer is added to the composition to plasticize the film and keep it flexible when it is applied to the skin. Finally, the antibacterial composition includes about 50 to 90 percent of a solvent which evaporates or penetrates the skin upon topical application to leave the plasticized polymeric film having the antibacterial compound in it against the skin. The resultant film resists water and wear, so frequent application of the formulation is not required.

Non water soluble polymeric compositions useful with this invention include ethylcellulose based polymers sold under the mark Aquacoat by FMC Corporation of Philadelphia, Pennsylvania; poly (methyl vinyl ether/maleic acid) polymers sold under the mark Gantrez by GAF Corporation; and copolymers of vinyl pyrrolidone and long chain -olefins sold under the mark Ganex by GAF. The Ganex polymer composition is preferred. These compositions are provided by the manufacturer containing certain solvents (e.g. alcohol) to make them workable in processing equipment. The solvent dries to leave a film when the polymer is applied to a surface on thin film. The polymers listed above are exemplary, other polymers compatible with the skin can also be used.

Antibacterial compounds which can be used in the formulation of this invention include erythromycin, tetracycline, clindamycin and meclccycline. Other bioactive agents (e.g., benzyl peroxide, retinoic acid, etc.) useful in treating skin conditions can also be included in the formulation When antibacterial agents are used, however, the formulation can be used to treat infections on or immediately under the skin, including acne.

A volatile solvent is also part of the formulation. The amount of solvent to be added depends on the amount of solvent in the polymeric material provided by the manufacturer, usually the amount of volatile solvent already in the polymeric material is insufficient, so some solvent is added to bring the total solvent content to within the 50 to 90 percent range indicated. Virtually any non-toxic, non-irritating solvent can be added. It is preferred that the polymer be soluble in the added solvent so that the formulation can be spread on the skin to produce an even, uniform film, and to prevent the product from separating into layers. However, the polymer can be emulsified or dispersed in the solvent with emulsifiers, if necessary, so the polymer need not be soluble in the solvent. The solvent either should be volatile so that the polymer dries to form a film on the skin, or the solvent should be absorbable into the skin to leave a film on the skin.

A plasticizer is added to the composition to make the film, when the solvent dries or is absorbed, flexible so it will resist cracking. An oily substance compatible with the skin can be used. However, some oily substances such as peppermint oil, eucalyptol oil, geranyl acetate or qeraniol not only are compatible with skin and plasticize the film but enhance the penetration of antibacterial agents into the skin. For this reason, the above named oils are preferred in this invention. Because geranyl acetate and geraniol are sweet smelling. they are the most preferred. However, in addition to the above named plasticizers, tributylcitrate, diethyl phthalate and diethyl sebecate can be used as plasticizers.

Preparation and formulation of compositions of this invention will be described in the specific examples which follow:

EXAMPLE 1

2% erythromycin
30% ethylcellulose
1% sodium lauryl sulfate
1% cetyl alcohol
4% tributylcitrate (plasticizer)
30% 190 proof ethanol
32% distilled water a) Ethylcellulose powder (30 gm) was dissolved in ethyl acetate (300 ml). Erythromycin (2 gm) was added to the mixture, and mixed thoroughly. The plasticizer, tributylcitrate (4 grams) was added to the mixture, and mixed thoroughly.

b) An aqueous solution of sodium lauryl sulfate (1 gm) and cetyl alcohol (1 gm) was prepared in distilled water (32 ml).

c) The two mixtures from a and b above were combined by adding mixture b dropwise into mixture a, the surfactant (sodium lauryl sulfate) aiding in the emulsification of b into a.

d) The combined mixture was placed in a rotary evaporator to remove the ethyl acetate.

e) The ethyl alcohol (30 ml; 190 proof) was then added to the suspension of fine spheres of ethyl cellulose which formed during the procedure described in a-d above. A milky-white suspension of medicament was obtained.

When applied, the water and alcohol either evaporate or penetrate the skin to leave a plasticized film of ethylcellulose. The water/alcohol mixture form the "solvent" phase indicated above.

EXAMPLE II 21.3% micronized ethylcellulose
0.7% cetyl alcohol
0.8% sodium laurel sulfate
2.0% erythromycin
4.0% diethylphthalate
25% ethanol
46.3% distilled water a) Aquacoat contains micronized ethylcellulose (30%), cetyl alcohol (1%), sodium laurel sulfate (1%) and 68% water. The aquacoat suspension (71 ml) was mixed with diethylphthalate (4 ml), a plasticizer. b) Erythromycin base (2.0 gm) was dissolved in 190 proof ethanol (25 ml). The mixture from part a was then added, and mixed well. A sufficient quantity of water was added to reach a final volume of 100 ml for the total mixture. A milky white suspension was produced.

EXAMPLE III 2.0% (m/v) erythromycin base
0.5% diethyl sebacate
93.5% ethanol
1.0% ethanol
1.0% 2-amino-2 methyl propanol (AMP)
5.0% ethyl monoesters of poly (methyl vinyl ether/maleic acid) polymer a) Gantrez ES 225 is a commercially available solution which contains 50% ethyl monoesters of poly (methyl vinyl ether/maleic acid) polymer and 50% ethanol. It is sold by GAF Corporation of Wayne, New Jersey. Gantrez ES 225 (10 ml) was mixed with ethanol (88.5 ml). Erythromycin base ( 2 gm) was then added.

b) AMP (1.0 ml) and diethyl sebacate (0.5 ml) were then added and mixed well with the mixture obtained from part a. AMP was added to neutralize the pH to about 7.0. Diethyl sebacate is a plasticizer. The resultant solution was clear.

EXAMPLE IV 2.0% (m/v) erythromycin base
5.5% polyvinyl pyrrolidone/hexadecene copolymer
94.0% isopropanol
0.5% diethyl sebacate Ganex V-516 is a commercially available resin containing 55% polyvinyl pyrrolidone/hexadecene copolymer and 45% isopropanol. It is sold by GAF Corporation of Wayne, N.J. Ganex V-516 (10 ml) was mixed with 89.5 ml isopropanol. Diethyl sebacate (.5 ml) was added, and mixed well. Erythromycin base (2 gm) was then added and mixed until a clear solution was obtained.

EXAMPLE V 4.0% (m/v) erythromycin base
5.5% polyvinyl pyrrolidone/hexadecene copolymer
94.0% isopropanol
0.5% diethylsebacate The above formulation was prepared in the same fashion as in Exhibit IV above, except 4 grams of erythromycin base were added instead of 2 grams.

EXAMPLE VI 2.0% (m/v) erythromycin base
10.0% geranyl acetate
84.5% isopropanol
5.5% polyvinyl pyrrolidone/hexadecene copolymer Erythromycin (2 gm) was added to isopropanol (80 ml) and geranyl acetate (10 ml), and mixed well until a clear solution was formed. Ganex V-516 (10 ml) was added, Ganex V-516 consisting of 55% polyvinyl pyrrolidone/hexadecene copolymer and 45% isopropanol. A clear solution resulted.

EXAMPLE VII 2.0% (m/v) erythromycin base
10.0% peppermint oil
84.5% isopropanol
5.5% polyvinyl pyrrolidone/hexadecene copolymer The formulation was prepared the same way as described in Exhibit VI, except peppermint oil was used instead of geranyl acetate.

EXAMPLE VIII-XV 2.0% (m/v) erythromycin base
10.0% plasticizer
84.5% isopropanol
5.5% polyvinyl pyrrolidone/hexadecene copolymer These formulations were prepared the same way VI, except the following plasticizers were used instead of geranyl acetate:

| | |
|---|---|
| Geraniol | (Example 8) |
| Trans-cinnamaldehyde | (Example 9) |
| (—)-carvyl propionate | (Example 10) |
| p-anisaldehyde | (Example 11) |
| (—)-carvyl acetate | (Example 12) |
| dl-menthylacetate | (Example 13) |
| (—)-menthone | (Example 14) |
| cinnamylalcohol | (Example 15) |

EXAMPLE XVI 2.0% (m/v) erythromycin base
5.0% geranyl acetate
89.5% isopropanol
5.5% polyvinyl pyrrolidone/hexadecene copolymer This formulation was prepared according to the procedure of Example VI, except a lesser amount (5%) of geranyl acetate and greater of solvent (89.5%) were used.

EXAMPLE XVII 2.0% (m/v) erythromycin base
1.0% geranylacetate
93.5% isopropanol
5.5% polyvinyl pyrrolidone/hexadecen copolymer This formulation was prepared according to the procedure of Example VI, except a lesser amount (1.0%) of geranyl acetate and a greater amount (93.5) of solvent were used.

EXAMPLE XVIII 2.0% (m/v) erythromycin base
0.0% geraniol
10.0% ganex V-216
80.0% 200 ethanol Ganex V-216 is a commercially available resin containing 100% active copolymer of polyvinyl pyrrolidone and hexadecene. It is sold by GAF Corporation of Wayne, New Jersey Erythromycin base (2 gm) was mixed with 80 ml 200 proof ethanol 10 ml geraniol was then added and mixed well. Then 10 ml ganex V-216 was added and mixed well.

EXAMPLE XIX 2.0% (m/v) erythromycin base
5.0% geraniol
10.0% ganex V-216
85.0% 200 proof ethanol Example XIX was prepared the same way as in Example XVIII, except different amounts of geraniol and ethanol were used.

EXAMPLE XX 2.0% (m/v) erythromycin base
5.0% geraniol
5.0% ganex V-216
90.0% 200 proof ethanol Example XX was prepared the same was as in Example XVIII, except different amounts of geraniol, ganex V-216 and ethanol were used.

EXAMPLE XXI 2.0% (m/v) erythromycin base
10.0% geraniol
5.0% ganex V-216
85.0% 200 proof ethanol Example XXI was prepared the same way as described in Example XVIII, except different amounts of anex V-216 and ethanol were used.

EXAMPLE XXII 2 0% (m/v) erythromycin base
2.0% geraniol
10.0% ganex V-216
88.0% 200 proof ethanol Example XXII was prepared the same way as described in Example XVIII, except different amounts of geraniol and ethanol were used.

EXAMPLE XXIII 2.0% (m/v) erythromycin base
10.0% geraniol
10.0% ganex V-216
80.0% isopropanol The formulation was prepared the same way as described in Example XVIII, except that isopropanol was used instead of ethanol.

It will be understood that various changes and modifications can be made in the details of procedure, formulation and use without departing from the spirit of the invention, especially as defined in the following claim.

We claim:

1. An antibacterial composition for topical administration comprising:
   a) from about 0.5 to about 10 percent of an antibacterial compound selected from erythromycin, tetracycline, clindamycin and meclocycline;
   b) from about one to about 30 percent of a non-water soluble, non-hydrogel forming polymeric composition selected from ethylcellulose, esters of poly(methylvinyl ether/maleic acid) polymers and polyvinyl pyrrolidone/hexadecene copolymers;
   c) from about 0.5 to about 40 percent of a penetration enhancing plasticizer selected from peppermint oil, geranyl acetate, geraniol, eucalyptol oil, trans-cinnamaldehyde, carvyl propionate, p-anisaldehyde, carvyl acetate, menthyl acetate, menthone and cinnamylalcohol said penetration enhancing plasticizer providing enhanced skin penetration of the antibacterial compound relative to a composition not comprising said penetration enhancing plasticizer;
   d) from about 50 to about 95 percent of a non-toxic nonirritating solvent in which said polymeric composition and plasticizer are dissolved;
   whereby upon topical application of said antibacterial composition, said solvent will evaporate or penetrate the skin and leave a thin protective film of polymeric composition which retains said antibacterial compound against the skin.

2. The antibacterial composition as recited in claim 1 wherein said penetration enhancing plasticizer is peppermint oil, geranyl acetate or geraniol.

3. The antibacterial composition as recited in claim 2 which comprises from about one to about ten percent penetration enhancing plasticizer.

4. The antibacterial composition as recited in claim 1 in which said non-water soluble, nonhydrogel forming polymeric composition is selected from esters of poly(methyl vinyl ether/maleic acid) polymers and polyvinyl pyrrolidone/hexadecene copolymers.

5. The antibacterial composition as recited in claim 1 wherein said solvent is selected from isopropanol and ethanol.

6. The antibacterial composition as recited in claim 1 wherein said antibacterial compound is erythromycin.

7. An antibacterial composition for topical administration, comprising:
   a) from about 0.5 to 10 percent of an antibacterial compound selected from erythromycin, tetracycline, clindamycin and meclocycline;
   b) from about one to about 30 percent of a non-water soluble copolymer of polyvinyl pyrrolidone and hexadecene comprising from about 20% to about 80% polyvinylpyrrolidone and from about 80% to about 20% hexadecene;
   c) from about 0.5 to about 40 percent of a penetration enhancing plasticizer which plasticizers said polymeric composition, said plasticizer selected from peppermint oil, eucalyptol oil, geranyl acetate and geraniol said penetration enhancing plasticizer providing enhanced skin penetration of the antibacterial compound relative to a composition not comprising said penetration enhancing plasticizer;
   d) from about 50 to about 95 percent of a non-toxic, non-irritating solvent in which said polymeric composition and plasticizer are dissolved;
   whereby upon topical application of said antibacterial composition, said solvent will evaporate or penetrate the skin and leave a thin protective film of polymeric composition which retains said antibacterial compound against the skin.

8. The antibacterial composition as recited in claim 7, wherein said antibacterial compound is erythromycin.

9. An antibacterial composition for topical administration comprising:
   a) from about one half to about 10 percent of erythromycin;
   b) from about one to about 30 percent of a non-water soluble polymeric composition comprising about 20% polyvinylpyrrolidone and about 80% hexadecene;
   c) from about one to about 10 percent of a penetration enhancing plasticizer which plasticizes said polymeric composition, said plasticizer selected from peppermint oil, eucalyptol oil, geranyl acetate and geraniol said penetration enhancing plasticizer providing enhanced skin penetration of the antibacterial compound relative to a composition not comprising said penetration enhancing plasticizer; and
   d) from about 50 to about 95 percent of a non-toxic non-irritating solvent in which said polymeric composition and plasticizer are dissolved;
   whereby upon topical application of said antibacterial composition, said solvent will evaporate or penetrate the skin and leave a thin protective film of polymeric composition which retains said antibacterial compound against the skin.

10. An antibacterial composition for topical administration, comprising:
   (a) from about 0.5 to about 10 percent of erythromycin;
   (b) from about one to about 30 percent of a copolymer comprising about 20% polyvinyl pyrrolidone and about 80% hexadecene;
   (c) from about one to about 10 percent of geraniol providing enhanced skin penetration of the erythromycin relative to a composition not comprising geraniol; and
   (d) from about 50 to about 95 percent of ethanol;
   whereby upon topical application of said antibacterial composition, said ethanol will evaporate or penetrate the skin and leave a thin protective film of the copolymer which retains the erythromycin against the skin.

11. The antibacterial composition as recited in claim 10 wherein the composition comprises 2% (m/v) erythromycin base; 10% geraniol; 10% copolymer; and 80% 200 proof ethanol.

* * * * *

UNITED STATES PATENT AND TRADEMARK OFFICE
CERTIFICATE OF CORRECTION

PATENT NO. : 5,082,656

DATED : January 21, 1992

INVENTOR(S) : Ho-Wah Hui; Chung-Chiang Hsu; Madhu K. Vadnere;

It is certified that error appears in the above-identified patent and that said Letters Patent is hereby corrected as shown below:

On title page, Column 2, line 6 of Abstract: replace "and polymeric" with --said polymeric--.

Column 6, line 20: replace "nonirritating" with --non-irritating--.

Column 6, line 34: replace "nonhydrogel" with --non-hydrogel--.

Signed and Sealed this

Twentieth Day of April, 1993

Attest:

MICHAEL K. KIRK

*Attesting Officer*  Acting Commissioner of Patents and Trademarks